(12) United States Patent
Schwimmer (10) Patent No.: US 9,888,938 B1
(45) Date of Patent: Feb. 13, 2018

(54) UVULA EXCISION DEVICE AND METHOD OF USE

(71) Applicant: The Snoring Center, Dallas, TX (US)

(72) Inventor: Craig Schwimmer, Dallas, TX (US)

(73) Assignee: The Snoring Center, Dallas, TX (US)

( * ) Notice: Subject to any disclaimer, the term of this patent is extended or adjusted under 35 U.S.C. 154(b) by 492 days.

(21) Appl. No.: 14/617,702

(22) Filed: Feb. 9, 2015

Related U.S. Application Data (60) Provisional application No. 61/937,549, filed on Feb. 9, 2014.

(51) Int. Cl.
| | |
|---|---|
| *A61B 17/24* | (2006.01) |
| *A61B 17/3205* | (2006.01) |
| *A61B 18/12* | (2006.01) |
| *A61B 17/00* | (2006.01) |
| *A61B 18/00* | (2006.01) |
| *A61B 17/32* | (2006.01) |

(52) U.S. Cl.
CPC ......... *A61B 17/3205* (2013.01); *A61B 17/24* (2013.01); *A61B 18/12* (2013.01); *A61B 2017/0023* (2013.01); *A61B 2017/00438* (2013.01); *A61B 2017/248* (2013.01); *A61B 2017/320064* (2013.01); *A61B 2018/00595* (2013.01)

(58) Field of Classification Search
CPC .............. A61B 17/24; A61B 17/22031; A61B 2017/306; A61B 2017/2212; A61B 2017/00287
See application file for complete search history.

(56) References Cited

U.S. PATENT DOCUMENTS

| | | | | |
|---|---|---|---|---|
| 4,817,602 A | * | 4/1989 | Beraha .................... | A61F 6/204 606/137 |
| 5,486,183 A | * | 1/1996 | Middleman ............ | A61B 10/02 606/113 |

\* cited by examiner

*Primary Examiner* — Victor Nguyen
(74) *Attorney, Agent, or Firm* — Bill R. Naifeh (57) ABSTRACT

Disclosed herein are embodiments and methods of use for a surgical excision device which contains a disposable hand-held instrument with a blade for severing a uvula and an attached net for capturing and removing the uvula.

6 Claims, 6 Drawing Sheets

UVULA EXCISION DEVICE AND METHOD OF USE

CROSS REFERENCE TO RELATED APPLICATIONS

This application claims the benefit of the filing date of U.S. provisional patent application Ser. No. 61/937,549, entitled "Uvula Excision Device," filed on Feb. 9, 2014, the disclosure of which is incorporated herein by reference for all purposes.

TECHNICAL FIELD

The invention relates in general to a surgical instrument for performing an uvulectomy, and in particular to a handheld surgical excision device for transection, retrieval, and removal of the uvula.

BACKGROUND INFORMATION

Snoring can have serious physical and psychological effects on the snorer and those around him which include lack of sleep, high blood pressure, and relationship problems. Snoring that is interrupted by episodes of obstructed breathing is known as obstructive sleep apnea. Serious episodes can reduce blood oxygen levels, causing the heart to pump harder. Many things can contribute to snoring and sleep apnea. There are a range of minimally invasive treatments available. One such treatment is removal of the uvula (uvulectomy).

Uvulopalatopharyngoplasty (UPPP) and laser-assisted uvulopalatoplasty (LAUP) are traditional surgical methods of removing the uvula. UPPP involves the removal of not only the uvula, but of adjacent palatal tissue as well. This is performed in an operating room, under general anesthesia, is considered to be quite morbid, and may cause major complications. This surgery is therefore performed infrequently. LAUP is less invasive modification of UPPP, which can be performed as an out-patient procedure. However, LAUP is still quite painful, and is also performed infrequently. "Simple" uvulectomy can be performed in the office, using local anesthesia, and is significantly less morbid than UPPP or LAUP. Uvulectomy is therefore often employed as an initial attempt at treatment, reserving more aggressive techniques for "treatment failures". One of the limiting factors in a surgeon's ability to comfortably and safely perform uvulectomy is that it requires the use of three separate instruments to be in the mouth at the same time. A first instrument holds the tongue down, a second instrument severs the uvula, while a third instrument grasps the uvula and then removes it after it has been severed. Grasping the uvula is essential, because if it is transected without grasping, it can fall into the patient's airway (aspirate), causing potentially fatal airway compromise. Preventing aspiration of the transected uvula is an important part of the safe performance of an uvulectomy.

What is needed is a single surgical excision device that severs, captures and removes the uvula, thereby eliminating the need for a third instrument in the mouth.

SUMMARY

In response to these and other problems, in one embodiment, there is a surgical excision device which contains a disposable handheld instrument with a blade for severing a uvula and an attached net for capturing and removing the uvula.

These and other features, and advantages, will be more clearly understood from the following detailed description taken in conjunction with the accompanying drawings. It is important to note the drawings are not intended to represent the only aspect of the invention.

DETAILED DESCRIPTION

For the purposes of promoting an understanding of the principles of the present inventions, reference will now be made to the embodiments, or examples, illustrated in the drawings and specific language will be used to describe the same. It will nevertheless be understood that no limitation of the scope of the invention is thereby intended. Any alterations and further modifications in the described embodiments, and any further applications of the principles of the inventions as described herein are contemplated as would normally occur to one skilled in the art to which the invention relates.

When directions, such as upper, lower, top, bottom, clockwise, counter-clockwise, are discussed in this disclosure, such directions are meant to only supply reference directions for the illustrated figures and for orientation of components in the figures. The directions should not be read to imply actual directions used in any resulting invention or actual use. Under no circumstances, should such directions be read to limit or impart any meaning into the claims.

Figure 1A:
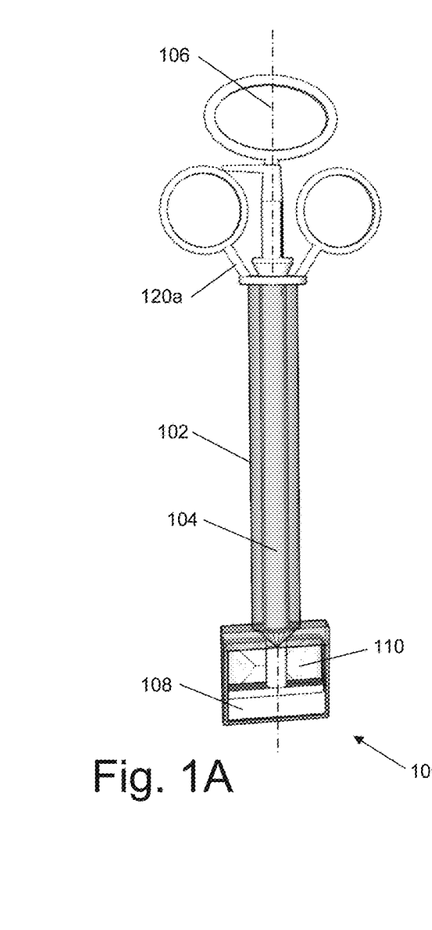
FIG. 1A is a top view illustrating the uvula excision device in an actuated position and FIG. 1B is the device of FIG. 1A in a pre-actuated position.
Figure 1B:
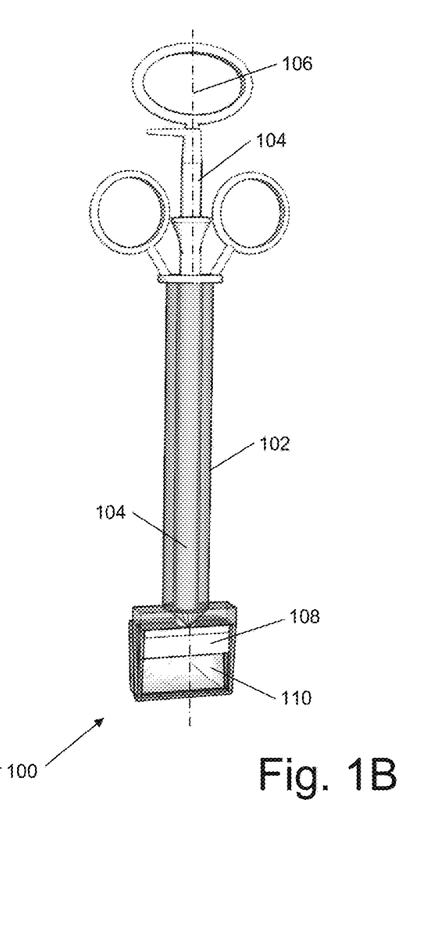

FIGS. 1A and 1B illustrates a top view of one embodiment of a uvula excision device 100. The device 100 is illustrated in an actuated or collapsed position in FIG. 1A. In contrast, in FIG. 1B the device is illustrated in a pre-actuated or extended position. The primary components of one embodiment of the uvula excision device 100 include a hollow outer cylinder or barrel 102, an inward movable shaft 104 having a longitudinal axis 106, a severing device, such as a blade 108 coupled to the movable shaft, and a uvula capturing mechanism, such as a net 110.

In certain embodiments, a biasing member (not shown), such as a helical spring, may be positioned laterally between the movable shaft 104 and the outer barrel 102 for longitudinally biasing the movable shaft to the pre-actuated or extended position shown in FIG. 1B. In other words, the biasing member exerts a longitudinal force on the movable shaft 104 to keep the movable shaft in the extended position. The biasing member may be made of any suitable sterile material for use in surgical application, such as a surgical metal. In yet other embodiments, such as the one illustrated in FIGS. 1A and 1B, the position of the movable shaft 104 is held in place by frictional forces between the movable shaft and the outer barrel 102 which may be easily overcome by the surgeon or user.

Figure 2A:
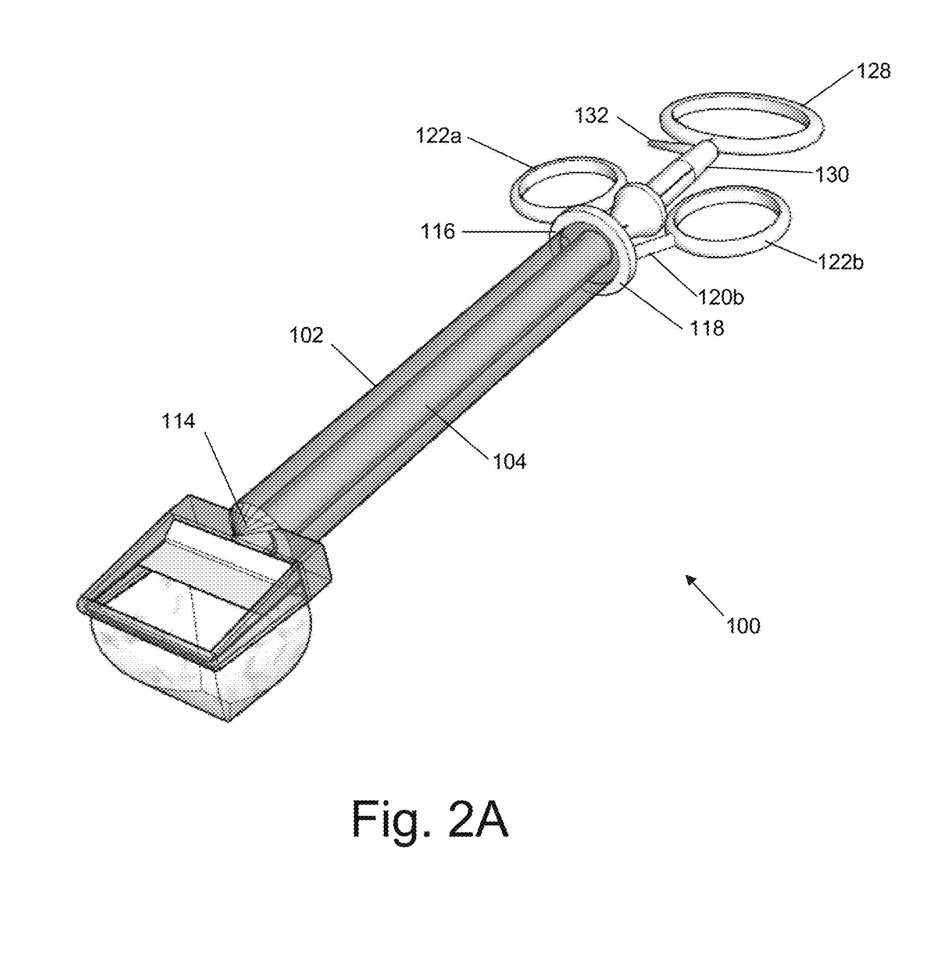
FIG. 2A is a perspective view illustrating one aspect of the assembled uvula excision device.
Figure 2B:
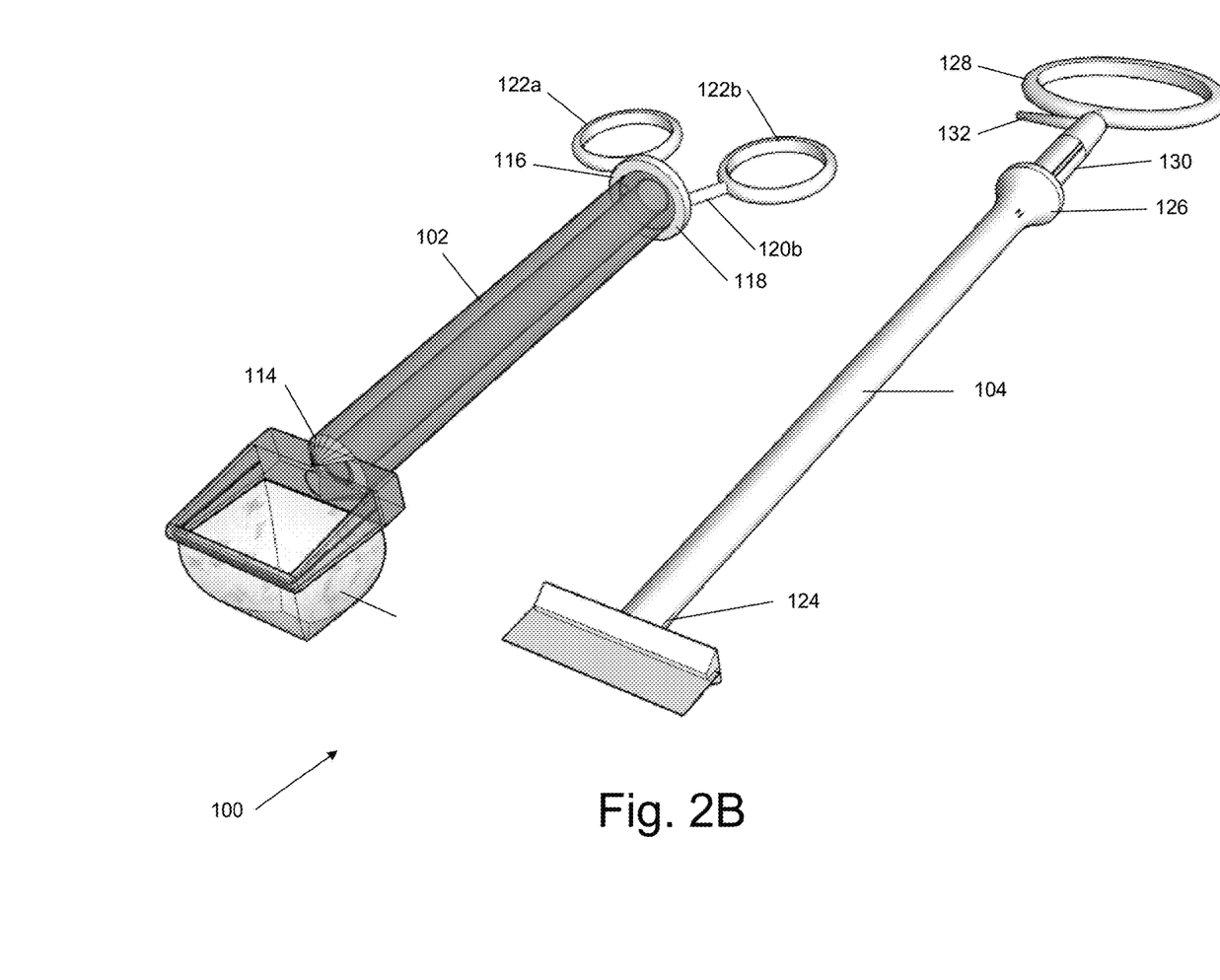
FIG. 2B is a perspective view showing some of the primary structural elements of the unassembled device illustrated in FIG. 2A.

FIG. 2A is a perspective view illustrating the assembled device 100. FIG. 2B is a perspective view illustrating the components of the device 100, specifically there is the inward movable shaft 104 illustrated apart from the outer barrel 102 so that details of the various components can be discussed. The outer barrel 102 has a distal end 114 and a proximal end 116. In certain embodiments, the outer barrel 102 may be made of a sterile plastic and may be molded from rigid plastic resins. If desired, the plastic may be transparent and may be formed by conventional molding methods, such as injection molding or 3D printing. In other embodiments, the outer barrel 102 can be fabricated out of a surgical metal where a more durable or reusable instrument is desired.

In the illustrated embodiment, the outer barrel 102 may act as a longitudinal guide for the movable shaft 104 and limit the lateral movement of the movable shaft when the shaft is moved from the extended position to collapsed position. The proximal end 116 of the outer barrel 102 may be coupled a lateral connecting ring or end stop 118. The end stop 118 may be coupled to two angled shanks 120*a* and 120*b*, which are in turn coupled to two finger rings 122*a* and 122*b*, respectively (See FIG. 1A for shank 120*a*). (In other embodiments, the two finger rings 122*a* and 122*b* may be directly coupled to the hollow barrel 102.) In certain embodiments, the end stop 118, angled shanks 120*a* and 120*b*, and finger rings 122*a* and 122*b* may be made from a surgical metal or from a plastic having the required tensile strength to overcome tensile forces placed on the angled shanks 120*a* and 120*b*. In yet other embodiments, the angled shanks 120*a* and 120*b* may be made from plastic and internally reinforced with a metal wire or frame. In other embodiments, the finger rings 122*a* and 122*b* may be replaced with finger grips or finger rests.

As illustrated in FIGS. 1A, 1B, and 2A, the movable shaft 104 may be partially located inside of the hollow outer barrel 102 in a concentric manner and has a diameter sized to allow a sliding movement within the hollow out barrel 102. Referring back to FIG. 2B, the movable shaft 104 has distal end 124 and a proximal end 126. In certain embodiments, the shaft diameter of the proximal end 126 may be enlarged to act as a stop which prevents the user from pushing the movable shaft too far longitudinally in the distal direction.

In certain embodiments, the movable shaft 104 may be coupled to a thumb rest, guide or ring 128 coupled to the proximal end 126 of the movable shaft via a connecting shaft 130. In some embodiments, the thumb ring 128 acts as an actuator to longitudinally move the movable shaft 104 within the hollow outer barrel 102. In certain embodiments, a shaft stop 132 may laterally extend from the connecting shaft 130 and be longitudinally located such that it abuts the finger ring 122*a* in the fully actuated position to prevent the user from longitudinally moving the movable shaft 104 too far in the distal direction.

Figure 5A:
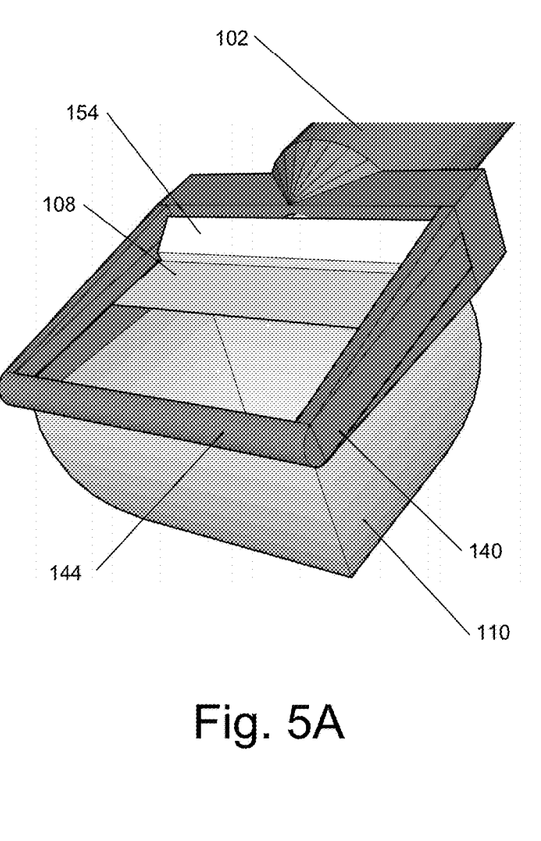
FIG. 5A is a perspective view of a cutting frame and retrieval portion of the device of FIG. 1A in a pre-actuated position.
Figure 5B:
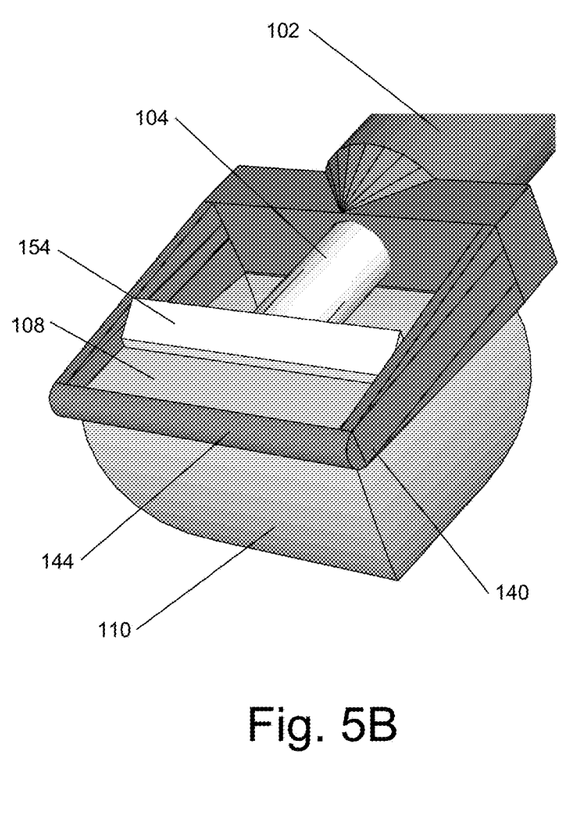
FIG. 5B is a perspective view illustrating a cutting frame and retrieval device of FIG. 5A in an actuated position.

In other embodiments the movable shaft 104 and outer barrel 102 may be coupled to another form of an actuator such as a love-kerrison handle actuator. In such an embodiment, the end stop 118 of the outer barrel 102 may be coupled to a proximal laterally extending handle which angles from the longitudinal axis in a proximal direction. The movable shaft 104 maybe coupled to a distal laterally extending handle which angles from the longitudinal axis in a distal direction. A pin positioned close to the end stop 118, but laterally away from the longitudinal axis 106, rotatably couples the distal laterally extending handle to the proximal laterally extending handle and creates a fulcrum for the distal laterally extending handle. Thus, a user can squeeze the distal handle in a proximal direction causing the handle to rotate about the pin. In turn, a lateral shank coupling the distal handle to the movable shaft 104 rotates about the pin and moves in the distal direction. This movement in the distal direction of the lateral shank in turn causes the movable shaft 104 to move in the distal direction from a pre-actuated or extended position as illustrated in FIG. 5A to a actuated or collapsed position as illustrated in FIG. 5B.

Figure 3:
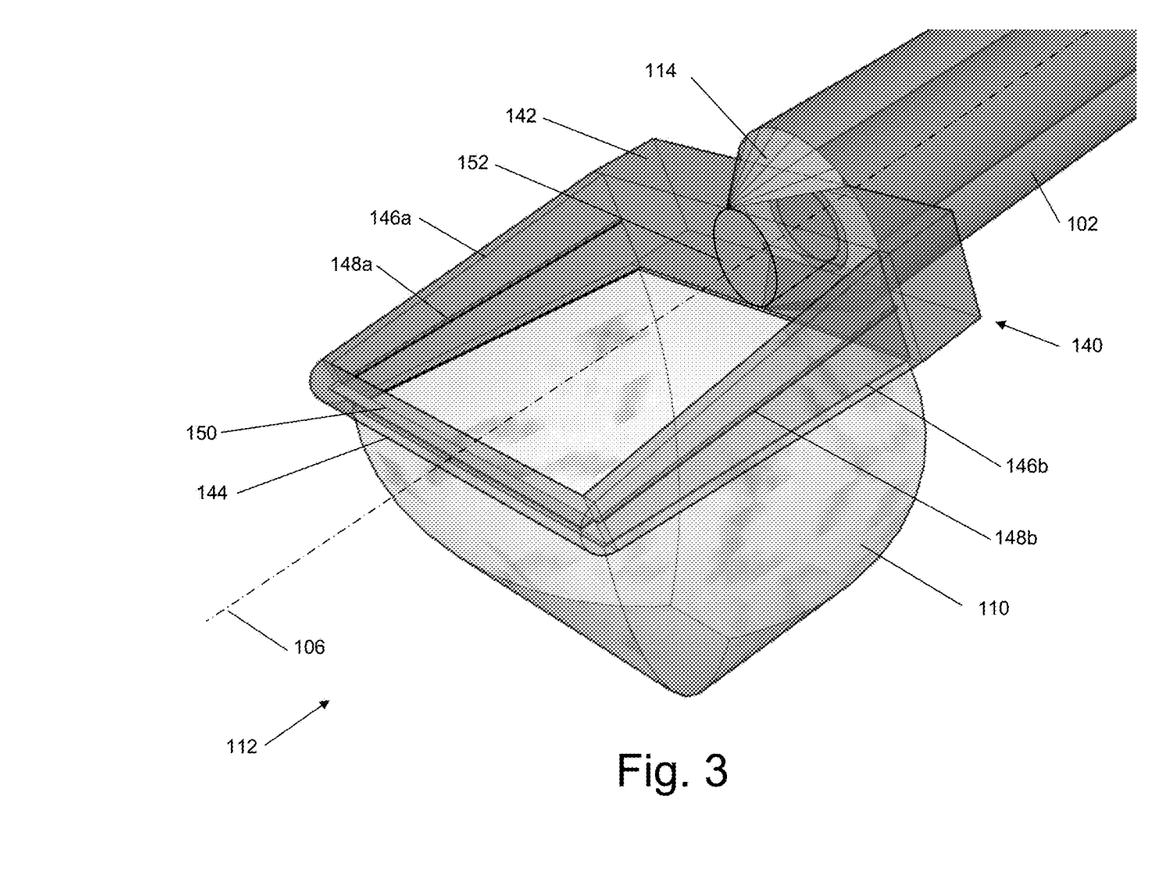
FIG. 3 is a detailed view of a retrieval mechanism which may be used with some aspects of the device illustrated in FIG. 2A.

FIG. 3 is a detailed perspective view of one embodiment of the retrieval mechanism 112 which may be coupled to the distal end 114 of the outer barrel 102. In some aspects the retrieval mechanism 112 comprises a frame 140. In the exemplary embodiment illustrated in FIG. 3, the frame 140 may be generally rectangular in shape, having a proximal frame member 142, a distal frame member 144, and two longitudinal frame members 146*a* and 146*b*. The proximal frame member 142 extends laterally outward from the longitudinal axis 106 to a width sufficient to easily capture a severed uvula. The distal frame member 144 extends laterally outward from the longitudinal axis 105 to a width that is generally similar to that of the proximal frame member 142. The longitudinal frame member 146*a* joins one end of the proximal frame member 142 to the corresponding end of the distal frame member 144. Similarly, the longitudinal frame member 146*b* joins the opposing end of the proximal frame member 142 to the corresponding opposing end of the distal frame member 144.

A longitudinal aperture 152 may be defined within the proximal frame member 142 having an diameter sufficient to allow the movable member 104 to slidingly move through the aperture 152. Longitudinal grooves 148*a* and 148*b* may be defined within the interior faces of the longitudinal frame members 146*a* and 146*b*, respectively. In certain embodiments, the longitudinal grooves 148*a* and 148*b* act as longitudinal guides to prevent lateral displacement or deflection of the blade 108 or a blade support (not shown in FIG. 3). There may also be a lateral groove 150 defined within the interior face of the distal frame member 144. The lateral groove 150 allows the blade to extend past the interior face of the distal frame member 144 which allows for a cleaner cut or severing of the uvula.

The sterile nylon or plastic bag or net 110 may be coupled to adjoining side faces of the members of the frame 140. Specifically the net 100 may extend laterally outwardly from the side faces of the proximal frame member 142, the distal frame member 144, and the longitudinal frame members 146*a* and 146*b*. The depth of the net 110 is sufficient to allow the easy capture of the severed uvula (e.g., approximately 1").

Figure 4:
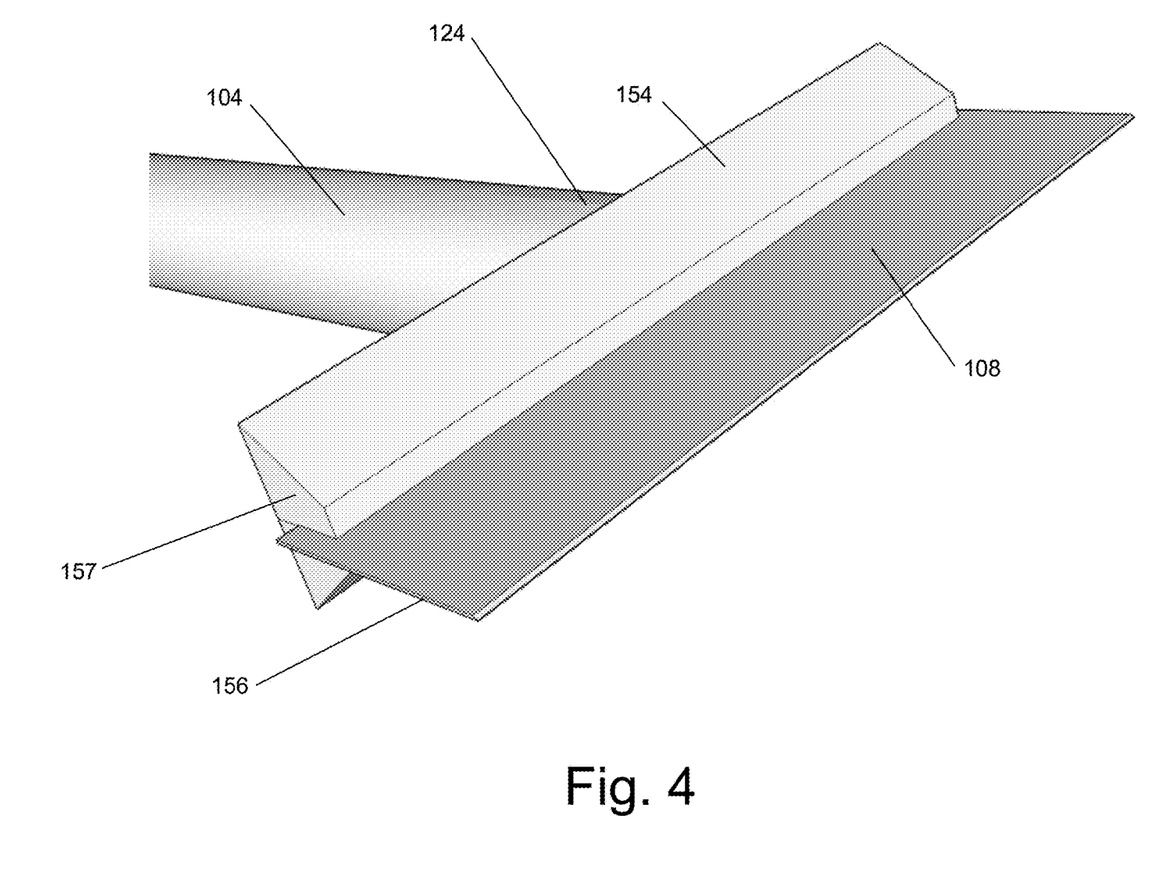
FIG. 4 is a perspective view of one embodiment of a blade which may be used with some aspects of the device illustrated in FIG. 2A.

FIG. 4 is a detailed perspective view of one embodiment of a blade 108 which may be coupled to the distal end 124 of the movable shaft 104. The movable shaft 104 may be slidingly coupled to and pass through the aperture 152 of the proximal frame member 142 (FIG. 3) to couple to a blade support 154 which engages the blade 108. In this exemplary embodiment, the exterior edges of the blade 108, such as edge 156, extend past the exterior edge 157 of the blade support 154 to engage the corresponding grooves 148*a* and 148b defined within the longitudinal frame members 146a-146b, respectively (see FIG. 3).

When the movable shaft 104 is manually actuated by, for instance, by a one-handed movement, the movable shaft moves longitudinally toward the distal end of the outer barrel 102. Because the blade 108 is coupled to the movable shaft 104 via the blade support 154, the blade moves from a proximal or pre-actuated position illustrated in FIG. 5A to a distal or actuated position illustrated in FIG. 5B, there providing a cutting action that severs the uvula when the uvula is positioned with the frame 140.

The frame 140 is coupled to the net 110 affixed to the bottom or side of the frame for retention of the uvula after it has been severed with the device 100. Thus, the uvula can be severed with one smooth actuating movement, then easily extracted from a patient's oral cavity.

Other embodiments may include a curved or pointed blade (not shown). If a curved or pointed blade is used, the distal frame member 144 would be either curved or pointed to follow the shape of the blade so that a "clean" cut can be made. The apex of the curved or pointed blade may occur along the longitudinal axis 106 and may extend distally away from the rest of the frame 140.

When the term "surgical metal" is used throughout this disclosure, the term includes, but is not limited any metal that can be used in a surgical environment such as stainless steel, aluminum, tungsten carbide, aluminum, and titanium.

Operation

Referring now to FIGS. 1 through 5B, one manner of using one embodiment of the present invention will now be described. The uvula excision device 100 provides for one-handed excision and extraction of the uvula.

In some procedures, a single dose of 8-10 mg of intravenous dexamethasone can be administered prior to surgery. Antibiotics are usually not necessary. In certain procedures, the patient may be given a local anesthetic if the patient does not have much of a "gag reflex" otherwise the patient may be placed under general anesthesia.

The surgeon may wear a headlight for illumination during the procedure. In some procedures, a mouth prop (McIvor or Crowe-Davis) may be used to gently open the oral cavity. The mouth prop may be secured to and suspended from a Mayo stand. Next, in certain procedures, an appropriately sized tongue blade may be used to retract the tongue without touching the posterior oropharyngeal wall. In certain procedures, the tongue and endotracheal tube may be positioned in the center of the tongue blade. If the tongue is particularly large, the blade may need to be repositioned during surgery (for instance, positioned once for removal of a first tonsil, followed by repositioning prior to removal of the other tonsil). In certain procedures, the hard palate may then be palpated for the presence of a submucosal cleft. If a submucosal cleft is present, the surgeon may decide not to remove the uvula because of the possibility of postoperative velopharyngeal insufficiency.

The distal end of device 100 may be inserted into the patient's oral cavity with the thumb ring 128 fully retracted in a pre-actuated configuration (as illustrated in FIGS. 1B and 5A). A physician may position the device 100 so that uvula is surrounded by the cutting frame 140 and the blade is in a pre-actuated position as illustrated in FIG. 5A. In one motion, the physician may fully push the thumb ring 128 distally thereby causing the blade 108 to move to an actuated position as illustrated in FIG. 5B, severing uvula and thus creating horizontal incision along the soft palate mucosa just anterior to the uvula and carried down through the mucosa through the muscularis uvulae, and the posterior mucosa, thus severing the uvula. Simultaneously, the severed uvula is captured in the net 110 thereby prohibiting complications from the severed uvula entering the patient's airway or into the esophagus. The device 100 may then be removed from the patient's oral cavity with the severed uvula contained in the net 110.

In certain procedures, hemostasis may be achieved using electrocautery. Conventional suturing techniques and materials may also be used as known in the art. For example, 2.0 Vicryl sutures may be used in a horizontal mattress fashion at the corners of the soft palate to bring the nasopharyngeal and oropharyngeal mucosa together in a single layer. The knot of the suture may be placed on the oropharyngeal surface.

Once the procedure is complete, the device 100 may be disposed of in a conventional manner if the device is designed to be disposal, otherwise once the severed uvula has been removed the, the device may be autoclaved.

Any advantages and benefits described may not apply to all embodiments of the invention. When the word "means" is recited in a claim element, Applicant intends for the claim element to fall under 35 USC 112, paragraph 6. Often a label of one or more words precedes the word "means". The word or words preceding the word "means" is a label intended to ease referencing of claims elements and is not intended to convey a structural limitation. Such means-plus-function claims are intended to cover not only the structures described herein for performing the function and their structural equivalents, but also equivalent structures. For example, although a nail and a screw have different structures, they are equivalent structures since they both perform the function of fastening. Claims that do not use the word means are not intended to fall under 35 USC 112, paragraph 6.

The foregoing description of the embodiments of the invention has been presented for the purposes of illustration and description. It is not intended to be exhaustive or to limit the invention to the precise form disclosed. Many combinations, modifications and variations are possible in light of the above teaching. Undescribed embodiments which have interchanged components are still within the scope of the present invention. It is intended that the scope of the invention be limited not by this detailed description, but rather by the claims appended hereto.

What is claimed is:

1. An surgical excision device for the removal and capture of a uvula, comprising:
    an outer hollow barrel having a distal end and a proximal end,
    a movable shaft positioned partially within and longitudinally slidingly coupled to the outer hollow barrel, the movable shaft having a distal end and a proximal end;
    a thumb ring coupled to the proximal end of the movable shaft;
    a cutting frame coupled to the distal end of the outer hollow barrel, the cutting frame having
    a proximal frame member extending laterally away from the outer hollow barrel,
    a distal lateral frame member having a lateral groove defined within a proximal face of the distal lateral frame member,
    a first longitudinal frame member coupling one exterior end of the proximal frame member to one exterior end of the distal lateral frame member, wherein the first longitudinal frame member has a first longitudinal groove defined within a first interior facing surface, a second longitudinal frame member coupling an opposing exterior end of the proximal frame member to an opposing exterior end of the distal lateral frame member, wherein the second longitudinal frame member has a second longitudinal groove defined within a second interior facing surface, a blade coupled to the distal end of the movable shaft and positioned within the cutting frame such that the blade is slidingly coupled to the first longitudinal groove and slidingly coupled to the second longitudinal grove such that upon actuation of the thumb ring, the blade moves longitudinally from a retracted position to an extended position, and a net coupled to one side of the cutting frame and sized to capture an excised uvula.

2. The excision device of claim 1, further comprising a first finger ring and a second finger ring coupled to the proximal end of the outer hollow barrel.

3. The excision device of claim 2, wherein the first finger ring and the second finger ring are formed from a surgical metal.

4. The excision device of claim 1, wherein the outer hollow barrel is formed from a sterile plastic.

5. The excision device of claim 1, wherein the movable shaft is formed from a sterile plastic.

6. The excision device of claim 1, wherein the blade is formed from a surgical metal.

\* \* \* \* \*